United States Patent [19]

Wegfahrt, Jr.

[11] Patent Number: 4,657,854

[45] Date of Patent: Apr. 14, 1987

[54] ASSAY SYSTEMS BASED ON MAGNESIUM-RESPONSIVE ENZYMES

[75] Inventor: Paul F. Wegfahrt, Jr., Camarillo, Calif.

[73] Assignee: Ivan Endre Modrovich, Camarillo, Calif.

[21] Appl. No.: 491,713

[22] Filed: May 5, 1983

[51] Int. Cl.[4] .......................... C12Q 1/54; C12Q 1/00; C12Q 1/48; C12Q 1/50; C12Q 1/42; C12Q 1/36; C12Q 1/32

[52] U.S. Cl. ............................................ 435/14; 435/4; 435/15; 435/17; 435/21; 435/24; 435/26

[58] Field of Search .................. 435/4, 14, 15, 17, 21, 435/24, 26, 810

[56] References Cited

U.S. PATENT DOCUMENTS 3,929,580  12/1975  Forgione et al. ..................... 435/17

FOREIGN PATENT DOCUMENTS 34213    8/1981  European Pat. Off. ................. 435/4
3141837  5/1983  Fed. Rep. of Germany .......... 435/4

Primary Examiner—Esther M. Kepplinger
Assistant Examiner—Shawn P. Foley
Attorney, Agent, or Firm—Christie, Parker & Hale

[57] ABSTRACT

There is provided an assay method for determining the concentration of magnesium ions in biological fluids. The method comprises the introduction of a sample of biological fluid to a magnesium-free assay solution containing at least one reactant and an enzyme capable of catalyzing a reaction with at least one reactant wherein the enzyme activity, and hence the rate of reaction, is partially or totally dependent on and correlatable to the concentration of magnesium that is present. The rate of reaction is measured by monitoring the loss of a detectable reactant or the formation of a detectable product.

14 Claims, 3 Drawing Figures

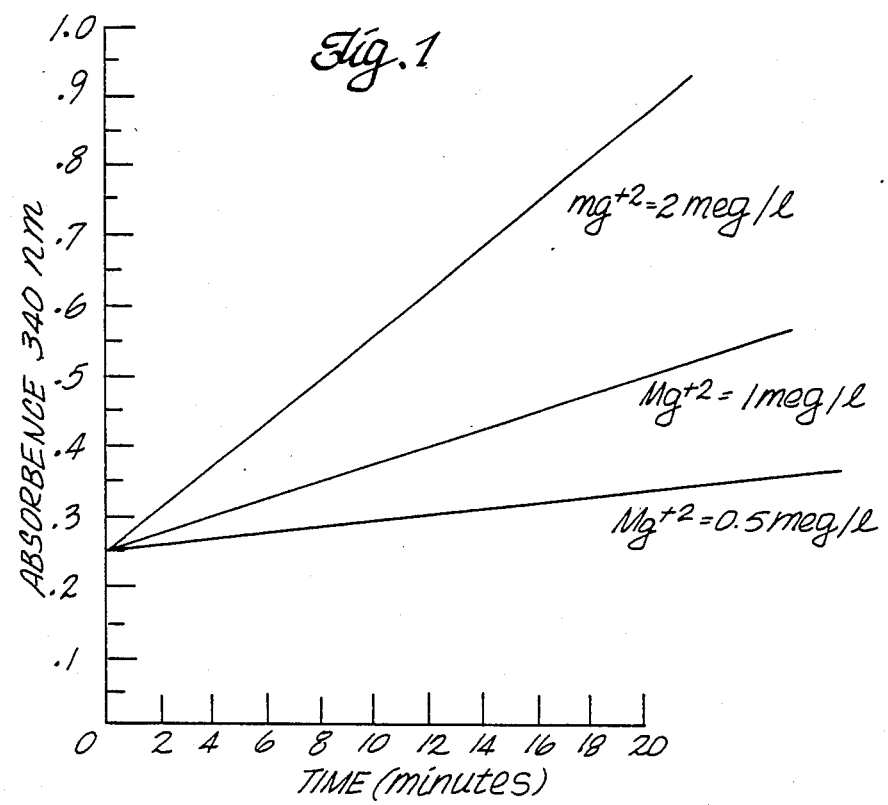
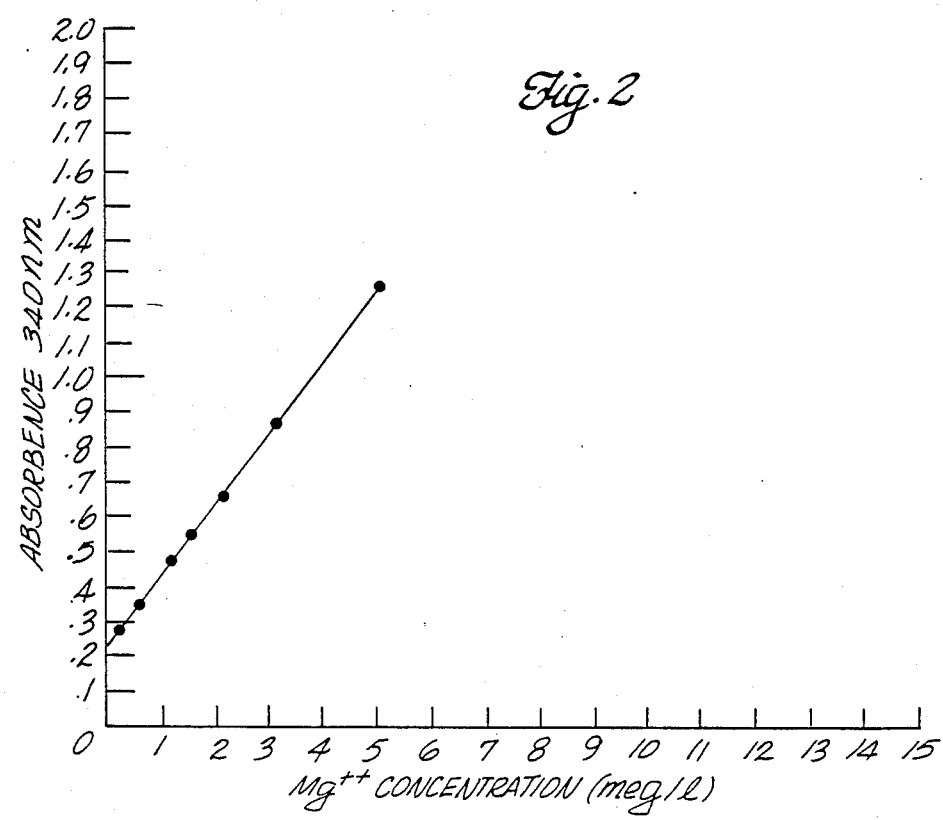

ASSAY SYSTEMS BASED ON MAGNESIUM-RESPONSIVE ENZYMES

BACKGROUND OF THE INVENTION

One of the most important minerals in biological tissue is magnesium. Many diseases can exist where magnesium-ion concentration is abnormally high or low. For example, decreased serum-magnesium ion levels may be encountered in various types of malnutrition, acute pancreatitis, alcoholism with delirium tremens, chronic glomerulonephritis, hyperthyroidism, hypoparathyroidism, hyperaldosteronism, and severe diarrhea. Serum-magnesium levels above the normal range may be found in uremia, vitamin D intoxication, and in pituitary dwarfs treated with human-growth hormone.

Of significant importance is magnesium-deficiency tetany, which has especially been found in alcoholic patients. It is characterized by low serum-magnesium-ion and normal serum-calcium levels. Probably the most important application for magnesium determinations in serum is in the treatment of this disease.

The most useful methods available for determining the concentration of magnesium ions in bodily fluids include atomic absorption, colorimetric methods, fluorometric methods, and by the precipitation of magnesium ammonium phosphate with the subsequent determination of phosphate by any of a variety of methods. Of these, atomic absorption spectrophotometry is the most accurate method, although it may be necessary to add lanthanum or strontium to overcome interferences. It requires, however, expensive instrumentation and relatively large samples.

Direct determination of magnesium-ion concentration may be made colorimetrically with the use of magnesiumindicator dyes, such as methylthymol blue, Titan Yellow (methylbenzothiazide-1,3-4,4'-diazo aminobenzol-2,2'-disulfonic acid), Calmagite [1-(1-hydroxy-4-methyl-2-phenalazo)-2-naphthol-4-sulfonic acid] and Magon [1-azo-2-hydroxy-3-(2,4-dimethylcarboxanilido)naphthalene-1(2-hydroxybenzene)]. For example, magnesium ions form a red lake with the dye Titan Yellow in an alkali solution. The absorbence of the solution against a standard is taken at the appropriate wavelength and the concentration of magnesium calculated according to Beer's Law. The method is simple and fast, but has accuracy only to within about 10 percent. Furthermore, the method follows Beer's Law for only a short range, thereby making it necessary to run multiple standards with each determination. In addition, there may be interferences in the serum sample, for example, from patients receiving calcium glucamate or mercurial diuretics, that lessen the accuracy of the method.

U.S. Pat. No. 3,754,864 describes a method using Calmagite which is simple and accurate but requires a long incubation time (20 minutes), and the working reagent is stable for only 24 hours.

Magnesium concentrations may also be determined by fluorometric methods. Magnesium will form a fluorescing complex with certain chelating agents such as 8-hydroxy5-quinoline sulfonic acid and o,o'-dihydroxyazobenzene. The complexes fluoresce when excited at an appropriate wavelength and the fluorescence can be measured. The method is simple and very sensitive. However, the method is not widely used, primarily because of the enhancing or quenching effect of other compounds that may be present.

There is a need for a simple, fast and inexpensive method for the determination of magnesium ions in serum and other biological fluids.

SUMMARY OF THE INVENTION

In accordance with the present invention, there is provided an assay method for the determination of magnesium in biological fluids. The method comprises combining a sample of the biological fluid with a magnesium-free enzyme assay solution. The enzyme assay solution contains at least one reactant and at least one magnesium-responsive enzyme which is capable of catalyzing a reaction involving a reactant to form at least one product, and wherein the rate of the reaction is dependent upon and is a known function of magnesium concentration. The rate of the reaction is determined normally by determining the rate of loss of at least one reactant or the rate of formation of at least one product. Knowledge of the rate of reaction establishes magnesium concentration in the biological fluid.

Any number of reactants and enzymes may be involved so long as the rate of at least one reaction is dependent upon magnesium-ion concentration. Usually, magnesium is required by the enzyme or enzymes to initiate the reaction.

In a preferred embodiment the assay solution comprises glucose, ATP and hexokinase. Hexokinase catalyzes a phosphorylation reaction wherein a phosphate group of the ATP is transferred to the glucose. The reaction is dependent upon the presence of magnesium, as magnesium forms an intermediate complex with the ATP coenzyme. The amount of magnesium present controls the rate of the enzyme reaction. The products of the reaction are glucose-6-phosphate (G-6-P) and ADP. Neither the reactants nor the products of this reaction is easily detectable.

The assay solution, therefore, further comprises the coenzyme nicotinamide-adenine dinucleotide (NAD) and the enzyme glucose-6-phosphate dehydrogenase (G-6-PDH). The G-6-PDH catalyzes a reaction between the formed G-6-P and NAD to thereby produce nicotinamide-adenine dinucleotide, reduced (NADH) and G-6-P. NADH is detectable as it absorbs ultraviolet radiation at 340 nm.

The concentrations of the components in the assay solution are such that the concentration of magnesium ions in the sample is rate-controlling. That is, the reactants are present in concentrations sufficiently large to not significantly affect the rate of the reaction over the time period involved in the analysis.

THE DRAWINGS

FIG. 1 is a graph showing the relationship between time and absorbence as a function of magnesium concentration based on the results of Example 1.

FIG. 2 is a graph showing the relationship between absorbence and magnesium-ion concentration after a fixed reaction time in accordance with Example 2.

Figure 3:
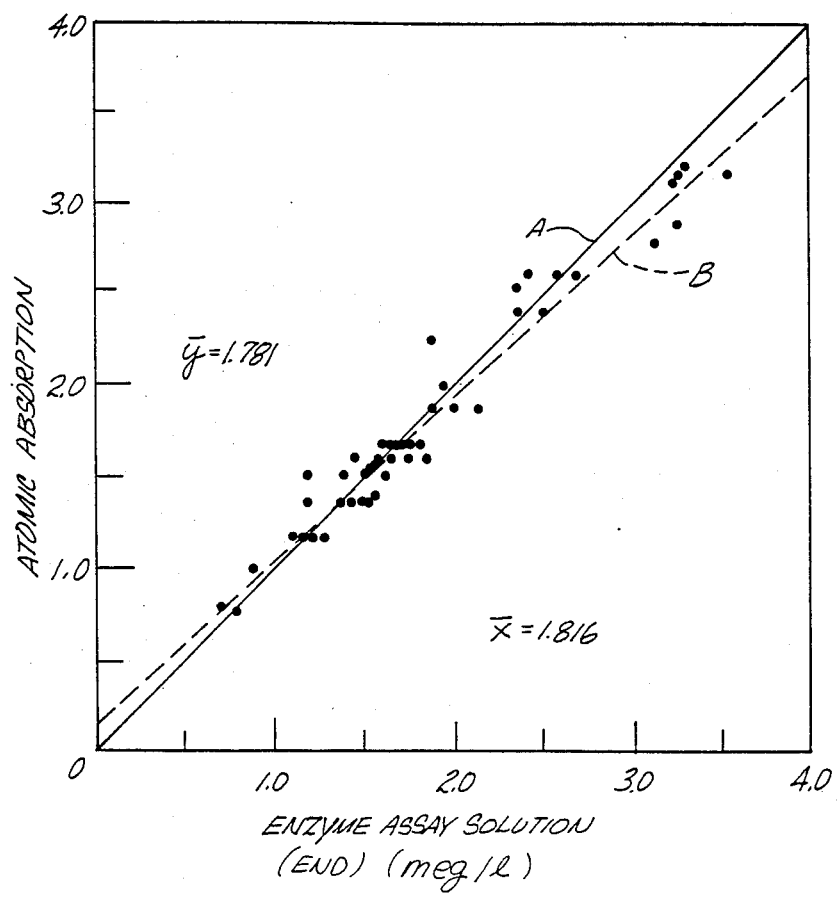

FIG. 3 correlates results of magnesium assay determination by practice of the instant invention to atomic absorption.

DETAILED DESCRIPTION

In accordance with the present invention, there is provided a process for the determination of magnesium concentration of body fluids or sera. The process comprises a clinical enzyme assay system in which the rate of loss of a detectable reactant or the rate of formation of a detectable product is directly dependent upon the activity of an enzyme, the activity of which, in turn, is dependent upon magnesium concentration. From correlations with atomic absorption, the system assays for total magnesium.

In the process, the amount of a detectable reactant or detectable product of an enzyme reaction is measured at a specified time or times after the enzyme reaction is initiated. The reaction is one wherein the enzyme activity is dependent upon magnesium concentration and in which the rate of reaction is dependent upon magnesium concentration, i.e., the concentration of magnesium limits the enzyme activity. The reaction is performed under conditions wherein the substrate and other necessary reactants are in abundance, and limits the rate of loss of the detectable reactant or the rate of production of the detectable product. Measurement of the reactant or product concentration at a specified time or times after the reaction is initiated is a measure of the rate of loss of detectable reactant or of production of the detectable product, and provides date which are correlated to magnesium concentration.

As used herein, the term "magnesium-free enzyme assay solution" or "enzyme assay solution" means a working solution of reagents including at least one enzyme, substrate and coenzyme in appropriate solvents as are needed to perform a clinical assay in which at least one enzyme is present for a reaction is responsive to magnesium and in which rate of the reaction is dependent upon magnesium concentration. The enzyme assay solution contains at least one ingredient which enables determination of the rate of a magnesium-initiated enzyme-catalyzed reaction. Magnesium, if present, is kept to its practical minimum concentration, and can be accounted for by running a blank sample.

Enzymes are macromolecules composed largely or entirely of proteins. They act as catalysts by initiating and/or increasing the rate of certain highly specific biological reactions. Enzymes are presently classified by their catalytic activity and substrate specificity.

As used herein, the term "substrate" refers to any molecule converted stoichiometrically to another molecule of different properties.

A "coenzyme" as used herein refers to a substrate which is regenerated by other enzymic reactions in a pathway to complete a cycle, and thus permits repeated use of a nucleotide moiety as part of its structure.

A large number of enzymes, especially those involved in the transfer of phosphate groups, have a partial or total requirement of magnesium ions in order to obtain full enzymic activity. For example, kinases are enzymes which catalyze the transfer of a phosphate group from ATP to a substrate. Mutases catalyze the transfer of phosphate groups at a low-energy level from one position on a substrate to another position on the same substrate. Both types of enzymes require magnesium for the phosphate transfer.

An enzymic-reaction sequence in which magnesium is required as exemplified by the following:

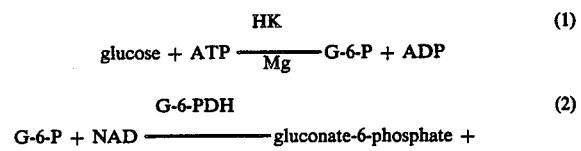

$$\text{NADH}^+ + \text{H}^+$$

wherein:
ADP=adenosine-5'-diphosphate
ATP=adenosine triphosphate
G-6-P=glucose-6-phosphate
G-6-PDH=glucose-6-phosphate dehydrogenase
HK=hexokinase
NAD=nicotinamide-adenine dinucleotide
NADH=nicotinamide-adenine dinucleotide, reduced
Mg=magnesium In the above reaction sequence, the phosphorylation of glucose (1) is the primary and the rate-determining reaction. The reaction rate may be limited by the reactant concentrations, including the glucose substrate and the coenzyme ATP, hexokinase enzyme concentration, and magnesium-ion concentration. In an assay solution of glucose, ATP and hexokinase, the magnesium concentration limits the rate of transfer of the phosphate group and, under conditions including sufficient concentrations of substrate, enzymes and coenzymes, limits the rate of formation of glucose-6-phosphate. Metals other than magnesium also promote the reaction. They include calcium, zinc, manganese and barium. Of these, manganese is the strongest activator for hexokinase, promoting approximately 30% of the enzyme activity as a comparable amount of magnesium. However, in most biological fluids the concentration of manganese is so low that it does not significantly affect the magnesium assay.

The reactants and products of the primary reaction are not easily determined. Therefore, to provide information relating to the primary reaction, a coupling or measuring reaction (2) is added to the assay system. The enzyme which catalyzes the coupling or measuring reaction (2) is glucose-6-phosphate dehydrogenase. Here, the rate of conversion of the coenzyme NAD to NADH is limited by the concentration of glucose-6-phosphate, which is rate-controlling when there are sufficient or excess NAD and glucose-6-phosphate dehydrogenase.

The reaction can be followed quantitatively using photometric methods of analysis. Photometric analysis is possible, as the coenzyme NADH exhibits an absorption at 340 nm and NAD does not. Hence, there are provided in an assay solution sufficient amounts of the glucose substrate, enzymes and coenzymes so that the conversion rate of NAD to NADH is a direct function of the concentration of magnesium. Thus, by measuring the rate or degree of formation of NADH as a function of time, or the degree of formation after a fixed time in the ultraviolet mode at 340 nm under these conditions, the magnesium concentration can be determined. Magnesium concentration in a sample of biological fluid may be determined as a function of the amount of NADH present in the system at a select time after initiation of the reaction sequence as compared to that amount produced with a control sample, i.e., a sample with a known concentration of magnesium. Preferably, to minimize the number of steps required, it is determined by measuring the rate of formation of NADH on a continuous or a multiple-point basis.

It is presently preferred to use the above-described glucose phosphorylation reaction and subsequent reduction of NAD comprising a clinical assay system for the determination of magnesium ions which comprises a substantially magnesium-free enzyme assay solution containing glucose, ATP, NAD, hexokinase and glucose-6-phosphate dehydrogenase, along with buffers, stabilizers and preservatives. Addition of a sample containing magnesium initiates the sequence of reactions leading to the production of NADH, which is detected.

Hexokinase is the presently preferred magnesium-responsive enzyme, and the amount of hexokinase affects the rate of reaction. Generally, a useful enzyme assay solution typically contains from about 100 IU/1 to about 10,000 IU/1 hexokinase in an aqueous buffered solution. The presently preferred hexokinase concentration is from about 500 IU/1 to about 2,000 IU/1.

Tris-hydroxymethyl aminomethane is the preferred buffer and is present to provide a 0.1 molar solution. If the buffered solution is greater than one molar, the tris-hydroxymethyl aminomethane can inhibit the enzyme reaction because of salt inhibition.

The enzyme glucose-6-phosphate dehydrogenase (G-6-PDH) is also present in the enzyme assay solution in an amount of from about 2,000 IU/1 or less, up to about 6,000 IU/1. Preferably, the G-6-PDH is present in an amount of from about 2,000 IU/1 to about 4,000 IU/1. Greater amounts than 6,000 IU/1 can be used, but no significant benefit is achieved and cost is increased. The lower limit is selected to convert the G-6-P formed from the glucose by the primary reaction as quickly as it is formed so that the first reaction is the overall rate-determining reaction for the two-reaction sequence.

A glucose is present in the enzyme assay solution in an amount of from about 10 mg/dl to about 1,000 mg/dl, preferably from about 50 mg/dl to about 200 mg/dl. The lower limit is set to insure that the glucose concentration is sufficient so as to not limit the rate of the primary reaction during the analysis, and normally in an excess amount.

The precursor to the enzyme assay solution may be provided in a lyophilized state or in liquid form. If provided in liquid form, it is necessary to separate the enzymes from the remainder of the reagents. As a minimum, therefore, a two-component kit is provided. One component is an enzyme reagent solution containing all of the enzymes, and the other, a substrate reagent solution containing the remaining constituents. The latter may be stabilized with a polyhydroxy organic compound containing from 2 to 4 hydroxyl groups and from 2 to about 10 carbon atoms. Polyhydroxy organic compounds include glycerol, ethylene glycol, sorbitol, mannitol, propylene glycol and the like. Glycerol is presently preferred. When a polyhydroxy organic compound is employed, the amount may range from about 5 to about 30 percent volume by volume in the enzyme assay solution.

Some substrates, e.g., glucose, may be prone to microbiological degradation, as they serve as a food source to bacteria, fungi and other microorganisms. Therefore, a bactericidal or fungicidal agent, preferably an azide compound such as sodium azide, is added, typically in an amount of about 0.1% w/w. However, the amount of azide or other bactericidal or fungicidal compound added can range from 0.01% to about 0.5%.

In addition to the foregoing, other bactericidal or fungicidal agents that do not chemically react with a substrate or inhibit the enzymatic reaction may be employed. For example, some of the agents which may be used in addition to sodium azide are benzoic acid, phenol, thymol or pentachlorophenol.

The presently preferred substrate solution contains the coenzymes NAD and ATP in an aqueous medium. They may be provided, if desired, as a third component.

The enzyme solution and the substrate-coenzyme solution, as prepared above, can be used in the clinical assay of magnesium ions when combined with the following-described coenzyme solution.

The coenzyme NAD may be present in the enzyme assay solution in an amount up to about 5 millimolar, and preferably from about 1 millimolar to about 3 millimolar. The NAD is generally added in considerable excess so there is always sufficient undegraded NAD present to insure that the concentration of NAD is not rate-limiting, even after several years of storage in liquid phase. ATP is provided in a concentration to be present in the enzyme assay solution in a concentration of from 0.5 or less to about 10 or more mM.

To perform clinical assay for magnesium ions, the enzyme reagent solution and the substrate-coenzyme reagent solution are combined to form a combined enzyme assay solution. Because of the difficulty of removing magnesium, the practical life of the combined enzyme assay solution is about one day at 4° C. The pH of the enzyme assay solution is from about 7.0 to about 8.0, and is preferably about 7.8.

The assay procedure using the enzyme assay solution of this invention may be used to determine magnesium-ion concentration in any number of biological fluids or sera. These include blood serum, urine and cerebrospinal fluid.

In practice, a selected volume of a magnesium standard or biological fluid sample containing magnesium ions is combined with a selected volume of the enzyme assay solution and mixed. This initiates the enzyme reactions. The mixture is typically introduced to a quartz cuvette, which is placed in a spectrophotometer. At a specified time or times after the initiation of the reaction, the absorbance at 340 nm is read and recorded.

The magnesium concentration is typically determined by locating the absorbance from the sample on a graph showing the absorbance of the standard(s) as a function of magnesium concentration. Alternatively, the absorbances from the sample and standard can be inserted into an equation, and the magnesium concentration calculated from the same. A typical equation would be:

$$\text{Mg concentration} = K \frac{\begin{pmatrix} \text{absorbance} \\ \text{of sample} \end{pmatrix} \begin{pmatrix} \text{concentration} \\ \text{of standard} \end{pmatrix}}{(\text{absorbance of standard})}$$

wherein K is a constant dependent upon the components of the assay solution and their concentrations and the volumes of the sample and assay solution.

Alternatively, the concentration of magnesium ions in the sample may be determined by measuring the absorbence at two or more recorded time intervals from the initiation of the reaction. The absorbence readings may be logged as points on a graph showing time as a function of absorbence wherein the slope of a line drawn through points thus generated is directly relatable to the reaction rate, and thus directly correlatable to a similarly determined rate for a standard of known magnesium concentration. All absorbances must be corrected for any background absorbance or reaction rate of the reagent above.

It is to be realized that only a preferred embodiment of the assay system has been described. A wide variety of assay systems can be generated, based upon the various enzymes that are responsive to magnesium-ion concentration. A partial list of magnesium-responsive enzymes and the reactions they catalyze is shown in Table 1.

TABLE 1

| ENZYME (e) | REACTION |
|---|---|
| acetate kinase | acetate + ATP $\overset{e}{\rightleftharpoons}$ acetyl phosphate + ADP |
| citrate lyase | citrate $\overset{e}{\rightleftharpoons}$ acetate + oxaloacetate |
| creatine kinase | creatine phosphate + ATP $\overset{e}{\rightleftharpoons}$ creatine + ATP |
| enolase | glycerate-2-phosphate $\overset{e}{\rightleftharpoons}$ phosphoenol pyruvate + $H_2O$ |
| F—6-P kinase | F—1,6-P + ATP $\overset{e}{\rightleftharpoons}$ F—1,6-DiP + ADP |
| gluconate kinase | gluconate + ATP $\overset{e}{\rightleftharpoons}$ G-6-P + ADP |
| hexokinase | glucose + ATP $\overset{e}{\rightleftharpoons}$ G-6-P |
| isocitrate dehydrogenase | isocitrate + NADP $\overset{e}{\rightleftharpoons}$ $\alpha$-keto glutarate + $CO_2$ + NADPH + $H^+$ |
| leucine amino peptidase FAD—pyrophosphorylase | FMN + ATP $\overset{e}{\rightleftharpoons}$ FAD + PPi |
| alkaline phosphotase phosphoglucomutase | G-1-P + G-1,6-DiP $\overset{e}{\rightleftharpoons}$ G-6-P + G-1,6-DiP |
| phosphoglyceryl kinase | glycerate-3-P + ATP $\overset{e}{\rightleftharpoons}$ glycerate-1,3-DiP |
| pyrophosphotase | $P_2O_7^{-7}$ + $H_2O$ $\overset{e}{\rightleftharpoons}$ $HPO_4^{-2}$ |
| pyruvate decarboxylase | pyruvate $\overset{e}{\rightleftharpoons}$ acetaldehyde + $CO_2$ |
| pyruvate kinase | pyruvate + ATP $\overset{e}{\rightleftharpoons}$ PEP + ADP |
| glycerol kinase | glycerol + ATP $\overset{e}{\rightleftharpoons}$ glycerol-1 + phosphate | wherein:
F-6-P=fructose-6-phosphate
F-1,6-DiP=fructose-1,6-diphosphate
FAD=flavin adenine dinucleotide
FMN=flavin mononucleotide
PPi=inorganic pyrophosphate
PEP=phosphoenol pyruvic acid
G-1-P=glucose-1-phosphate
G-1,3-DiP=glucose-1,3-diphosphate
NADP=nicotinamide adenine dinucleotide phosphate
NADPH=nicotinamide adenine dinucleotide phosphate, reduced
glycerate-3-P=glycerate-3-phosphate
glycerate-1,3-DiP=glycerate-1,3-diphosphate Lyophilized precursors and fluid assay kits used in the invention have protracted shelf-lives. Where, however, formulated into an enzyme assay solution, shelf-life is reduced to about 1 day in consequence of the normal practical inability to eliminate all magnesium.

EXAMPLE 1

A solution was prepared which comprised about 4 mM ATP, about 3 mM NAD, more than 1,000 IU/l hexokinase, about 3,000 IU/l G-6-PDH, along with buffers, stabilizers and preservatives. To 1 milliliter of the assay solution were added 25 microliters of a 4% glucose solution and 25 microliters of a 2 mg/l magnesium-acetate solution. The absorbence at 340 nm was recorded over selected time intervals. The data were logged on a graph of "time versus absorbence", which generated the line shown in FIG. 1. A straight line was generated through the points indicating a constant rate of reaction, the slope of the line being an indication of the reaction rate.

The procedure was again followed using magnesium acetate solutions of 1.0 mg/l and 0.5 mg/l concentrations. The measurements were logged on the above-mentioned graph and, again, straight lines were generated, as shown in FIG. 1, indicating constant rates of reaction. Accordingly, the slope of each line generated indicated a particular reaction rate and particular magnesium concentration, i.e., NADH formation as a function of time, was correlatable to the concentration of magnesium ions, wherein higher slope values indicated higher magnesium-ion concentrations because of a faster rate of reaction.

EXAMPLE 2

A magnesium-free assay solution was prepared as in Example 1. To 1 milliliter of the assay solution, 25 microliters of a 4% glucose solution and 25 microliters of a standard magnesium-acetate solution of known concentration were added. The absorbance at 340 nm was recorded 15 minutes after the addition of the standard magnesium-ion solution. The absorbance value thus generated was logged as a point on a graph of "absorbance versus magnesium-ion concentration", as shown in FIG. 2. The procedure was repeated using various concentrations of magnesium ion. A straight line was generated through the points, indicating a directly-correlatable relationship between the absorbance after 15 minutes and magnesium-ion concentration.

EXAMPLE 3

An enzyme assay solution was formulated in a proportion of 25 microliters of a 4% glucose solution to 1 milliliter of the assay solution of Example 1. The performance of the enzyme assay solution was correlated against magnesium determination using atomic absorption on blood sera from 54 patients. Atomic absorption measurements were made by an independent laboratory, and measurements using the enzyme assay solution were made in accordance with Example 1. The results are shown in FIG. 3. Line "A" has a slope of 45°. Line "B" is the line of best statistical fit. Correlation coefficient was 0.980. The equation of the regression was:

Atomic Absorption=0.892 enzyme assay solution+0.162.

What is claimed is:

1. A method for determining the concentration of magnesium in biological fluids which comprises:
    (a) combining a predetermined amount of a biological fluid with a predetermined amount of a substantially magnesium free enzyme assay solution comprising at least one reactant and at least one enzyme capable of iniating a reaction with said reactant contained in the solution leading to the formation of a product, to form a mixture wherein an enzymatically controlled reaction occurs, the rate of which is dependent upon the amount of magnesium introduced by the bilogical fluid;
    (b) determining the rate of reaction; and
    (c) establishing magnesium concentration in the biological fluid from the determined rate of reaction.

2. A method as claimed in claim 1 wherein an analytically-detactably reactant is reactant is present in the assay solution and the rate of reaction is measured by consumption of detactable reactant.

3. A method as claimed in claim 1 wherein said product formed is analytically detectable and the rate of reaction is measured by formuation of the detectable product.

4. A method for determining the concentration of magneisum ions in biological fluids which comprises:
    (a) combining a predetermized amount of a biological fluid with a predetermined amount of a substantially magnesium-free assay solution comprising at least one reactant and at least one enzyme having an enzymatic activity dependent on magnesium concentration and capable of initiating a reaction with said reactant present in the solution leading to at least one product, to form a mixture in which the reaction is initiated and the rate of reaction is controlled by the activity of the enzyme as a function of magnesium concentration in the mixture;
    (b) determining the rate of reaction; and
    (c) establishing the magnesium-ion concentration in the biological fluid from the determined rate of reaction.

5. A method as claimed in claim 4 wherein an analytically-detectable reactant is present in the assay solution and the rate of reaction is measured by consumption of detectable reactant.

6. A method as claimed in claim 4 wherein said product formed is analytically detectable and the rate of reaction is measured by formation of the detectable product.

7. A method for determining the concentration of magnesium in biological fluids which comprises:
    (a) combining a predetermined amount of a biological fluid with a predetermined amount of a substantially magnesium-free assay solution comprising at least one reactant and at least one enzyme having a reaction-promoting activity dependent on magnesium concentration to initiate a reaction with said at least one reactant leading to formation of an analytically-detectable product wherein the magnesium introduced by the biological fluid controls the rate at which the detectable product is formed;
    (b) measuring the amount of detectable product formed after at least one selected period of time; and
    (c) determining the magnesium concentration as a function of the amount of detectable product formed after such a period of time.

8. A method as claimed in claim 7 wherein the assay solution comprises a first enzyme which catalyzes a first enzyme reaction leading to at least one first non-detectable product wherein the rate of the first enzyme reaction is dependent upon the concentration of magnesium introduced by the biological fluid and wherein the assay solution further comprises at least one additional enzyme which catalyzes at least one additional enzyme reaction with at least one first non-detectable product leading to a detectable product wherein the rate of formation of detectable product is a function of the rate of formation of the first non-detectable product.

9. A method for determining the concentration of magnesium in biological fluids which comprises:
    (a) combining a predetermined amount of a biological fluid with a predetermined amount of a substantially magnesium-free assay solution comprising at least one analytically-detectable reactant and at least one enzyme having a reaction-promoting activity dependent upon magnesium concentration to initiate a reaction with said at least one analytically-detectable reactant leading to at least one product wherein the magnesium introduced by the biological fluid controls the rate at which the detectable reactant is consumed;
    (b) measuring the amount of detectable reactant after at least one selected period of time; and
    (c) determining the magnesium concentration as a function of the amount of detectable reactant consumed after such period of time.

10. A method for determining the concentration of magnesium in biological fluids which comprises:

(a) combining a predetermined amount of an aqueous substantially magnesium-free enzyme assay solution comprising glucose, ATP, NAD, hexokinase and G-6-PDH with a predetermined amount of a biological fluid containing magnesium to initiate the reaction sequence:

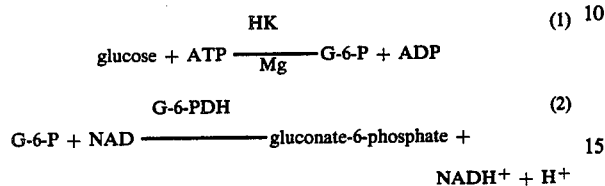

wherein:
ADP=adenosine-5'-diphosphate
ATP=adenosine triphosphate
G-6-P=glucose-6-phosphate
G-6-PDH=glucose-6-phosphate dehydrogenase
HK=hexokinase
NAD=nicotinamide-adenine dinucleotide
NADH=nicotinamide-adenine dinucleotide, reduced; and (b) determining the rate of formation of NADH+ and determining magnemium introduced by the biological fluid from the rate of formation of NADH+.

11. A method for determining the concentration of magnesium in biological fluids which comprises:

(a) combining a predetermined amount of an aqueous buffered substantially magnesium-free enzyme assay solution having a pH of from about 7.0 to about 8.0 and comprising glucose present in a concentration of from about 10 to about 1,000 mg/dl, ATP present in a concentration of from about 0.5 to about 10 mM, NAD present in a concentration of up to about 5 mM, hexokinase present in a concentration of from about 100 to about 10,000 IU/1, and G-6-PDH present in a concentration of from about 2,000 to about 6,000 IU/1 with a predetermined amount of a biological fluid containing magnesium to initiate the reaction sequence:

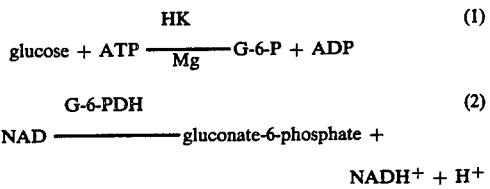

wherein:
ADP=adenosine-5'-diphosphate
ATP=adenosine triphosphate
G-6-P=glucose-6-phosphate
G-6-PDH=glucose-6-phosphate dehydrogenase
HK=hexokinase
NAD=nicotinamide-adenine dinucleotide
NADH=nicotinamide-adenine dinucleotide, reduced;

(b) determining the rate of formation of NADH+ and determining the concentration of magnesium introduced by the biological fluid from the rate of formation of NADH+.

12. A method as claimed in claim 10 in which the magnesium-free enzyme assay solution is buffered with tris-hydroxymethyl aminomethane present in a concentration of about 0.1 molar.

13. A method as claimed in claim 12 in which glucose is present in a concentration of from about 50 to about 200 mg/dl.

14. A method as claimed in claim 13 in which G-6-PDH is present in a concentration of from about 2,000 to about 4,000 IU/I.

* * * * *